US012667273B2

(12) United States Patent
Aoyagi et al.

(10) Patent No.: US 12,667,273 B2
(45) Date of Patent: Jun. 30, 2026

(54) NASAL ADAPTER

(71) Applicant: NIHON KOHDEN CORPORATION, Tokyo (JP)

(72) Inventors: Takayuki Aoyagi, Tokorozawa (JP); Toshiki Aoki, Tokorozawa (JP); Kenichiro Kabumoto, Tokorozawa (JP); Fumihiko Takatori, Tokorozawa (JP); Yuya Baba, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 652 days.

(21) Appl. No.: 18/180,473

(22) Filed: Mar. 8, 2023

(65) Prior Publication Data

US 2023/0293842 A1 Sep. 21, 2023

(30) Foreign Application Priority Data

Mar. 18, 2022 (JP) ................................. 2022-044028

(51) Int. Cl.
  *A61B 5/083* (2006.01)
  *A61B 5/097* (2006.01)
  *A61M 16/06* (2006.01)
(52) U.S. Cl.
  CPC ............ *A61B 5/0836* (2013.01); *A61B 5/097* (2013.01); *A61M 16/0672* (2014.02); *A61M 2230/432* (2013.01)

(58) Field of Classification Search
  CPC .. A61B 5/0836; A61B 5/097; A61M 16/0666; A61M 16/0672; A61M 2230/432
  See application file for complete search history.

(56) References Cited

U.S. PATENT DOCUMENTS

| | | | | |
|---|---|---|---|---|
| 2017/0007795 A1* | 1/2017 | Pedro | ..................... | A61B 5/082 |
| 2017/0035979 A1* | 2/2017 | Pedro | ................... | A61G 13/121 |
| 2019/0224435 A1* | 7/2019 | Pedro | ..................... | A61B 5/097 |
| 2019/0298960 A1* | 10/2019 | Kabumoto | ............ | A61B 5/082 |
| 2022/0031981 A1* | 2/2022 | Aoyagi | ............ | A61M 16/0009 |

FOREIGN PATENT DOCUMENTS

JP 2020-092749 A 6/2020

* cited by examiner

*Primary Examiner* — Joseph D. Boecker
(74) *Attorney, Agent, or Firm* — McDonald Hopkins LLC

(57) ABSTRACT

A nasal adapter includes a first portion and a second portion. The first portion includes a mouth exhalation guide portion having a facing portion facing a mouth of a living body and formed with a mouth-side guide path for guiding exhaled breath exhaled from the mouth to the facing portion, a base portion disposed above the mouth exhalation guide portion with respect to the living body, and a cuttable portion integrally formed with the mouth exhalation guide portion and the base portion. The cuttable portion disconnectably connects the mouth exhalation guide portion to the base portion. The base portion is fixed to the second portion. The first portion is detachably connected to the second portion at a connecting section below the cuttable portion with respect to the living body.

11 Claims, 7 Drawing Sheets

*FIG.3*

NASAL ADAPTER

CROSS-REFERENCE TO RELATED APPLICATIONS

The present application claims priority from Japanese Patent Application No. 2022-044028, filed on Mar. 18, 2022, the entire content of which is incorporated herein by reference.

TECHNICAL FIELD

The presently disclosed subject matter relates to a nasal adapter, and more particularly to a nasal adapter for measuring exhaled breath exhaled from mouth or nose of a living body.

BACKGROUND ART

In a recent year, a nasal adapter has been put into practical use for measuring exhaled breath exhaled from mouth or nose of a living body. The nasal adapter is attached to a face of the living body, and includes, for example, a mounting portion for mounting a sensor for measuring concentration of carbon dioxide contained in exhaled breath, and a mouth exhalation guide portion arranged to face the mouth on a lower side of the mounting portion. The mouth exhalation guide portion is formed to guide the exhaled breath exhaled from the mouth toward the sensor, and the sensor can sequentially measure the concentration of carbon dioxide contained in the exhaled breath.

SUMMARY

A nasal adapter of the related art that can measure concentration of exhaled gas from a mouth connects a mouth exhalation guide portion that collects exhaled breath from the mouth to a base portion where a gas sensor can be attached, and detects the gas concentration at the base portion. Also, this nasal adapter made it possible to move a position of the mouth exhalation guide portion by connecting the base portion and the mouth exhalation guide portion with a support shaft. However, when the mouth exhalation guide portion is connected to the base portion via the support shaft, the base portion, the mouth exhalation guide portion, and the support shaft need to be manufactured separately, resulting in an increase in the number of components. In JP2020-92749A filed earlier, a mechanism is realized in which the base portion and the mouth exhalation guide portion are integrally connected and a distance between the mouth exhalation guide portion and the mouth can be adjusted.

By the way, depending on a patient who attaches the nasal adapter, there are cases where it is easier to treat without the mouth exhalation guide portion. In this regard, the nasal adapter of JP2020-92749A has room for improvement.

According to an aspect of the present disclosure, there is provided a nasal adapter includes a first portion and a second portion. The first portion includes a mouth exhalation guide portion having a facing portion facing a mouth of a living body and formed with a mouth-side guide path for guiding exhaled breath exhaled from the mouth to the facing portion, a base portion disposed above the mouth exhalation guide portion with respect to the living body, and a cuttable portion integrally formed with the mouth exhalation guide portion and the base portion. The cuttable portion disconnectably connects the mouth exhalation guide portion to the base portion. The base portion is fixed to the second portion. The first portion is detachably connected to the second portion at a connecting section below the cuttable portion with respect to the living body.

BRIEF DESCRIPTION OF DRAWINGS

FIG. 3 is a right side view of the first portion of the nasal adapter according to the embodiment of the presently disclosed subject matter.

DESCRIPTION OF EMBODIMENTS

Hereinafter, an embodiment of the presently disclosed subject matter will be described with reference to the accompanying drawings. In the present application, when a nasal adapter is attached to a face of a living body, a head direction of the face is defined as the top, a jaw direction is defined as the bottom, a direction in which the face faces is the front, and an opposite direction is defined as the back. In addition, in drawings showing the face of the living body, the right is described as the right, and the left is described as the left. This is the opposite of left and right as viewed from a living body side.

Figure 1:
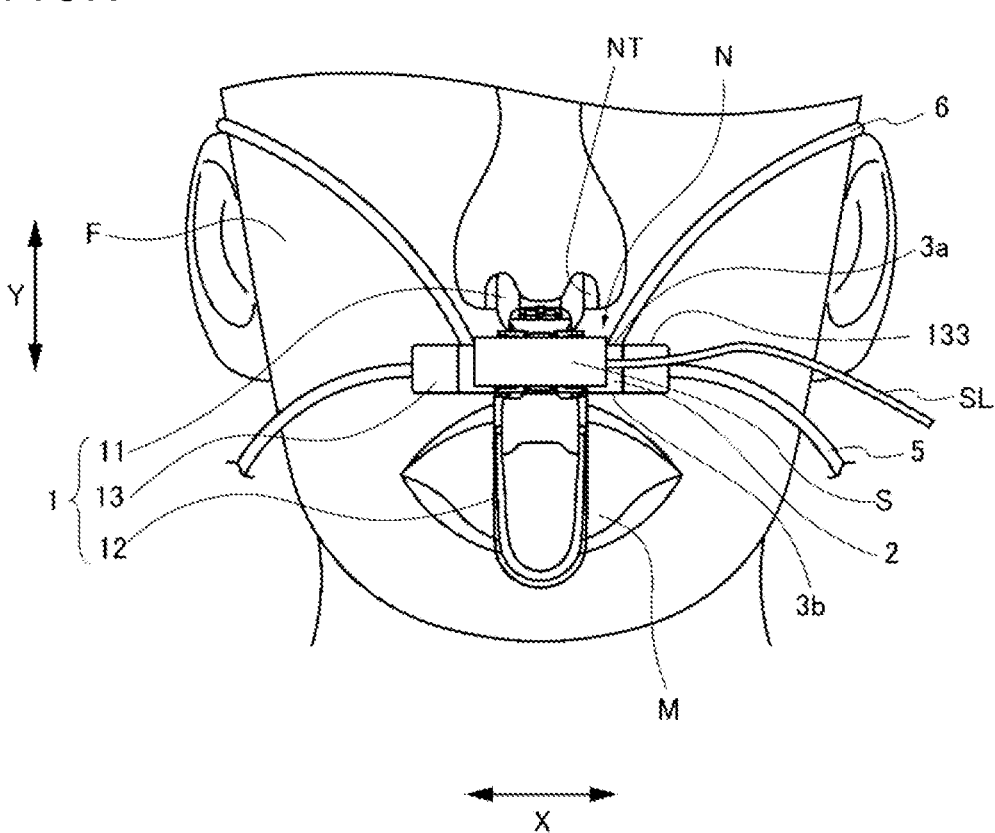
FIG. 1 is a diagram illustrating a nasal adapter applied to a living body according to an embodiment of the presently disclosed subject matter.

FIG. 1 illustrates a configuration of a respiratory management device provided with a nasal adapter N according to the embodiment of the presently disclosed subject matter. This respiratory management device is attached to a face F of a living body, and has the nasal adapter N, a pair of nasal cannulas 5, a fixing band portion 6, and a sensor S. FIG. 1 illustrates a state in which the nasal adapter N is applied to a subject as the living body to measure exhaled breath.

The nasal adapter N has a first portion 1 arranged in front of the face F and a second portion 2 attached in front of the first portion 1. The first portion 1 includes a nasal exhalation guide portion 11 arranged corresponding to a nostril NT of the living body, a mouth exhalation guide portion 12 arranged corresponding to a mouth M of the living body, and a base portion 13 disposed between the nasal exhalation guide portion 11 and the mouth exhalation guide portion 12. Here, the first portion 1 has flexibility and is integrally formed as a first member with a flexible material. Examples of the flexible material include vinyl chloride resin.

The nasal exhalation guide portion 11 guides exhaled breath exhaled from the nostril NT to the second portion 2, and is formed to branch and extend from the base portion 13 toward the two nostrils NT. The base portion 13 is arranged so as to extend in a right-left direction X with respect to the living body, and is formed so as to be able to attach the second portion 2 so as to cover a central portion thereof from the front. The base portion 13 is formed so that the nasal cannulas 5 can be respectively attached to right and left side portions, and the fixing band portions 6 can be attached to the right and left sides thereof. The mouth exhalation guide portion 12 guides the exhaled breath exhaled from the mouth M to the second portion 2 and is formed so as to extend in an up-down direction Y on the front side of the mouth M.

The second portion 2 holds the sensor S for measuring the exhaled breath guided from the nasal exhalation guide portion 11 and the mouth exhalation guide portion 12, and is formed so that the sensor S can be attached and detached. The second portion 2 is formed to have higher stiffness than the first portion 1. The second portion 2 is arranged in front of the base portion 13 of the first portion 1. The second portion 2 is attached to the base portion 13 and supports the base portion 13 made of a flexible material by its rigidity. The second portion 2 can be made of, for example, thermoplastic resin. This second portion 2 forms a measuring member. The sensor S is attached to the second portion 2 and optically measures concentration of carbon dioxide contained in the exhaled breath guided inside the second portion 2. A sensor line SL is led out from the sensor S to be connected to a body of a measuring device (not illustrated).

The pair of nasal cannulas 5 each have a tubular shape. One ends of the pair of nasal cannulas 5 are respectively attached to right and left connection heads 133 of the base portion 13 in order to supply a predetermined gas to the living body, which is the subject. The nasal cannulas 5 extend to a gas supply device (not illustrated) that supplies a predetermined gas, and the other ends of the nasal cannulas 5 are connected to the gas supply device. As the gas supply device, for example, one that supplies oxygen can be used. In the nasal adapter N, by providing a space between the first portion 1 and the second portion 2, a gas supply port 3a that opens upward toward the nostril NT and a gas supply port 3b that opens downward toward the mouth M are formed. Oxygen guided to the base portion 13 by the nasal cannula 5 is discharged around the nostril NT through the gas supply port 3a and around the mouth M through the gas supply port 3b. The fixing band portion 6 is for fixing the nasal adapter N to the face F of the living body, extends to surround the face F, and has both ends attached to the base portion 13.

Figure 2:
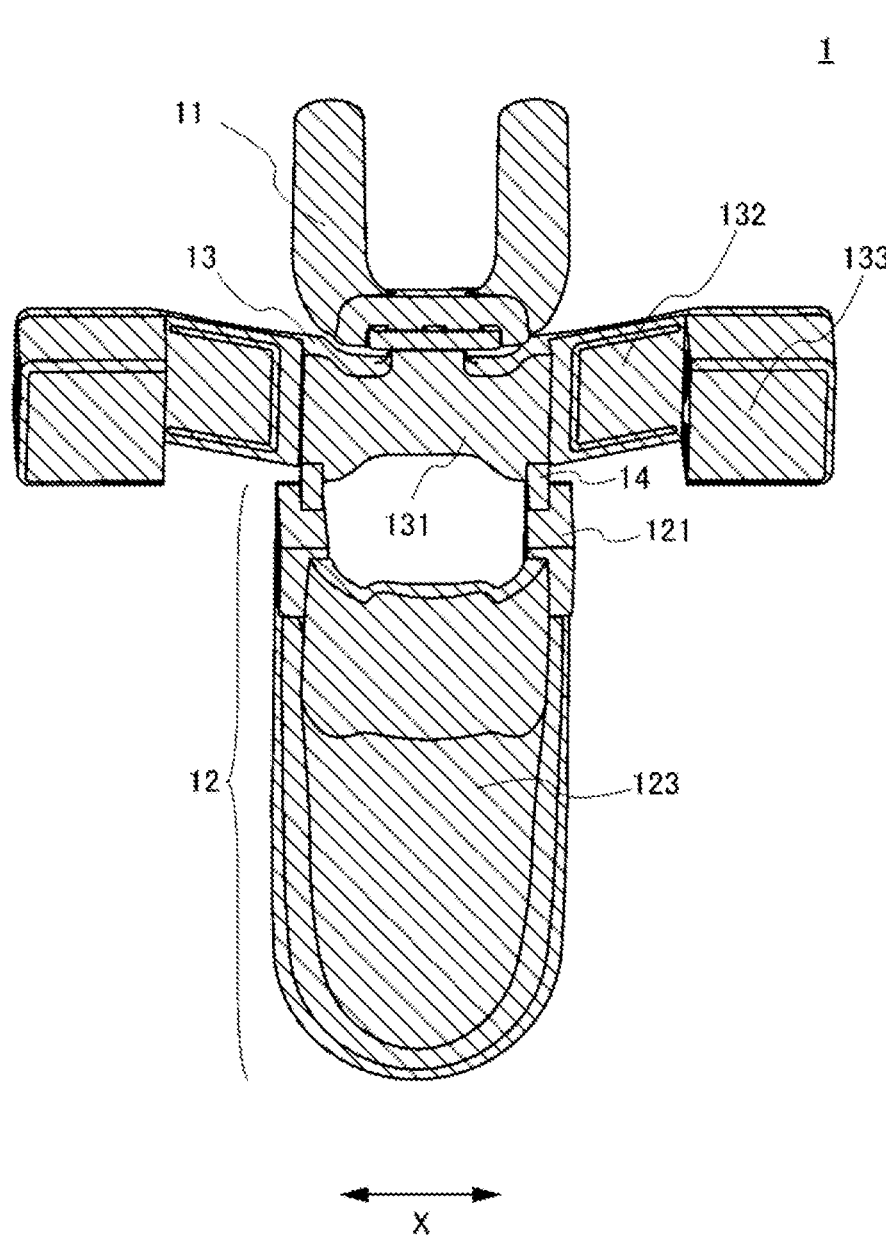
FIG. 2 is a diagram of a first portion of the nasal adapter according to the embodiment of the presently disclosed subject matter, viewed obliquely from above.
Figure 3:
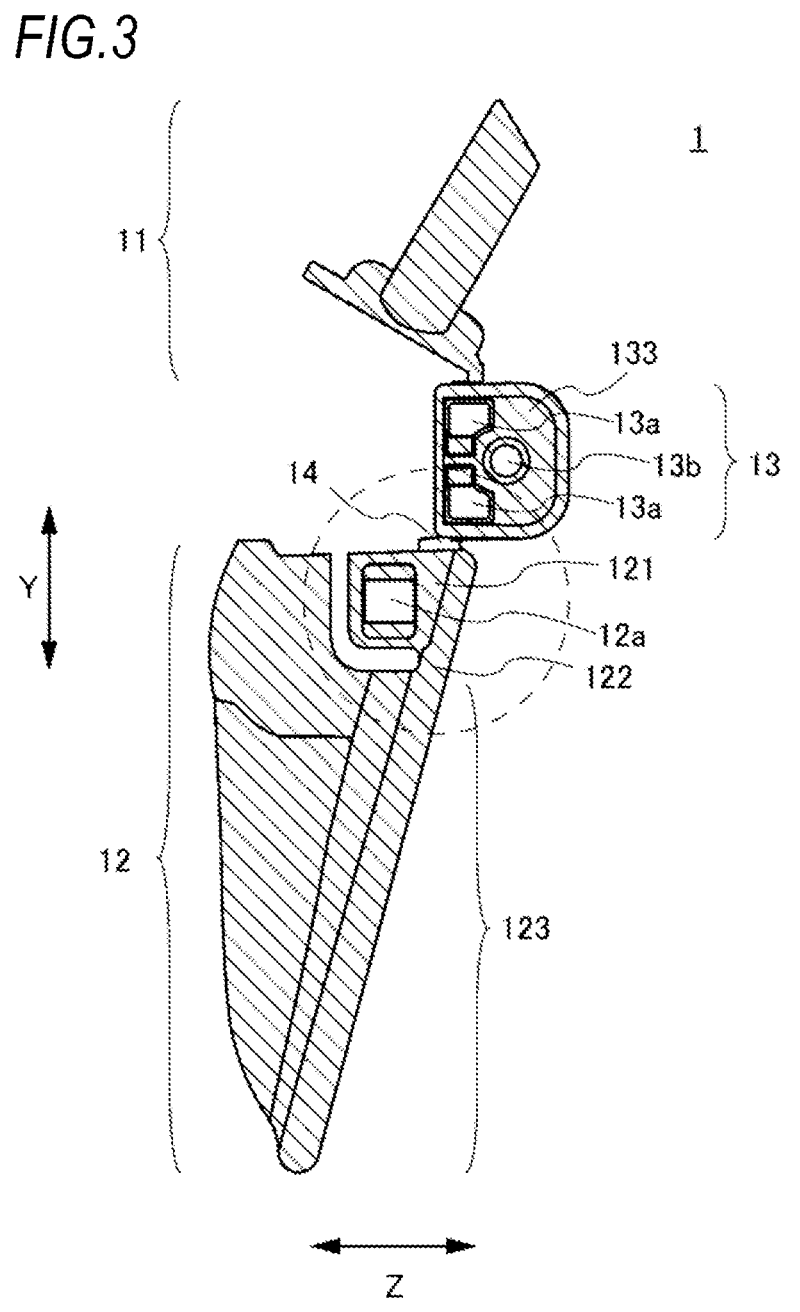

Next, a configuration of the nasal adapter N will be described in detail. The nasal adapter N has the first portion 1 and the second portion 2. First, the first portion 1 will be described. As illustrated in FIGS. 2 and 3, in the first portion 1, the nasal exhalation guide portion 11 is integrally connected to an upper portion of the base portion 13, and the mouth exhalation guide portion 12 is integrally connected to a lower portion of the base portion 13 via a cuttable portion 14.

As illustrated in FIG. 2, the base portion 13 is provided with a central base portion 131 at a center in the right-left direction X, with supply back portions 132 on right and left sides thereof, and further with the connection heads 133 further on the right and left sides thereof. A front surface of the supply back portion 132 is inclined obliquely rearward from the central base portion 131. The cuttable portions 14 are connected to the right and left of a lower portion of the central base portion 131.

As illustrated in FIG. 3, the mouth exhalation guide portion 12 has a connecting section 121, a bendable portion 122, and a facing portion 123 in order from the top, and the connecting section 121 is connected to the cuttable portion 14. The base portion 13 has the connection heads 133 on the right and left sides, and each connection head 133 includes two upper fixing holes 13a and a cannula hole 13b for connecting the nasal cannula 5. Also, each of the two connecting sections 121 has a lower fixing hole 12a.

As illustrated in FIG. 2, the connecting sections 121 are arranged on a pair of side portions of the mouth exhalation guide portion 12 and integrally connected to the base portion 13 via the cuttable portions 14. The mouth exhalation guide portion 12 is connected to the base portion 13 only by a pair of cuttable portions 14, and the part therebetween is separated from the base portion 13 without being connected. The cuttable portion 14 disconnectably connects the mouth exhalation guide portion 12 to the base portion 13 at two right-left positions on an upper side of the mouth exhalation guide portion 12 with respect to the living body. As illustrated in FIG. 3, each of the two connecting sections 121 is connected to the facing portion 123 by the bendable portion 122 on a rear side, and is separated from the facing portion 123 at other locations. Specifically, the connecting section 121 and the facing portion 123 are cut in the up-down direction Y and a front-rear direction Z to form an L-shaped notch, leaving the bendable portion 122 at the rear portion. The connecting section 121 of the mouth exhalation guide portion 12 is connected to the facing portion 123 by the bendable portion 122 on a side opposite to the cuttable portion 14 when viewed from the connecting section 121.

Figure 4:
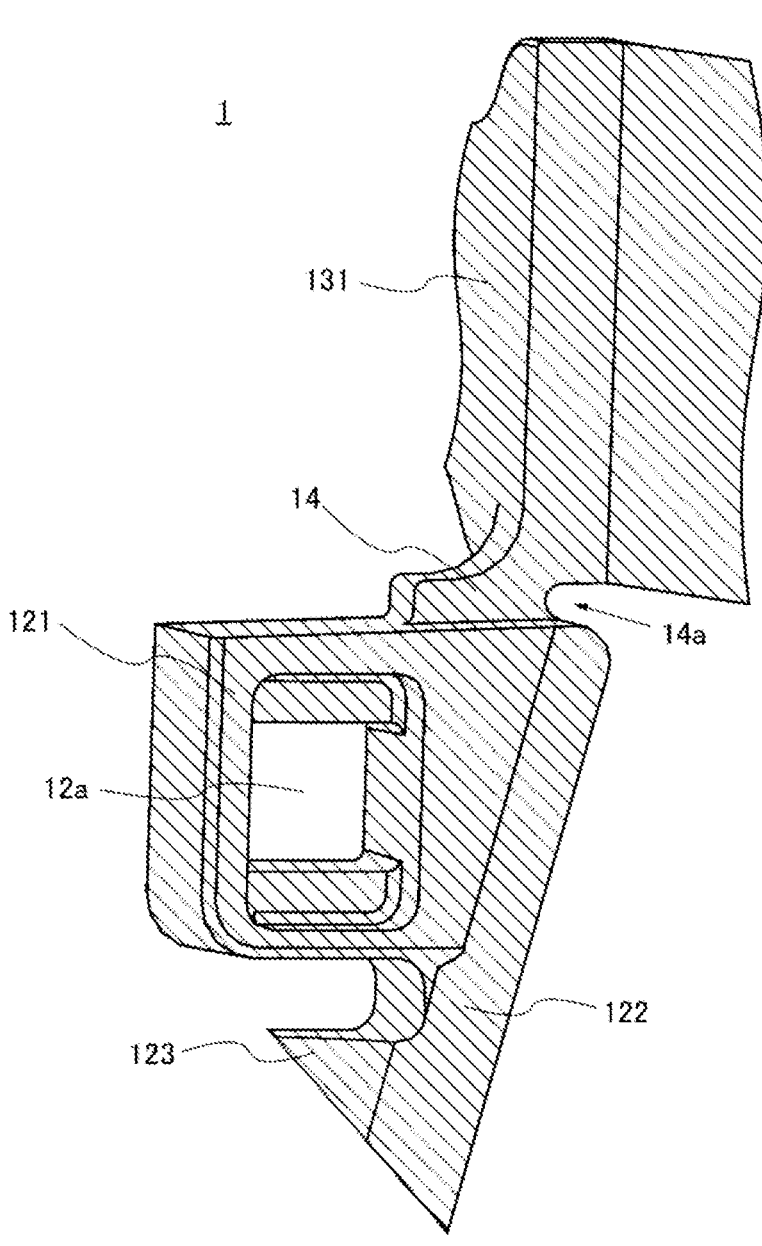
FIG. 4 is an enlarged perspective view of a cuttable portion of the first portion of the nasal adapter according to the embodiment of the presently disclosed subject matter.

The facing portion 123 is formed in a cup shape that curves forward and is arranged so as to face the mouth M of the living body. Here, the cuttable portion 14 is formed thinner than the base portion 13 and the connecting section 121 in a vicinity of the connection, and has a structure that is easy to cut. The cuttable portion 14 is formed narrower in the right-left direction X than portions of the mouth exhalation guide portion 12 and the base portion 13 near the cuttable portion 14. FIG. 4 is an enlarged view of a portion circled by a dotted line in FIG. 3 and viewed from an oblique direction, illustrating the cuttable portion 14 in an easy-to-see manner. The cuttable portion 14 is formed with a notch 14a that is cut forward from vicinities of the cuttable portion 14 in the mouth exhalation guide portion 12 and the base portion 13, and it is formed so as to narrow obliquely downward and rearward from an upper surface of the cuttable portion 14. The cuttable portion 14 may be made of a material that is weaker than the mouth exhalation guide portion 12 and the base portion 13, and may be configured to connect the mouth exhalation guide portion 12 and the base portion 13 so as to be cuttable. However, in the embodiment, the material of the cuttable portion 14 is the same as that of the mouth exhalation guide portion 12 and the base portion 13. The cuttable portion 14 has a thin portion with a small cross-sectional area, and is capable being torn off by hand due to its thinness.

Figure 5:
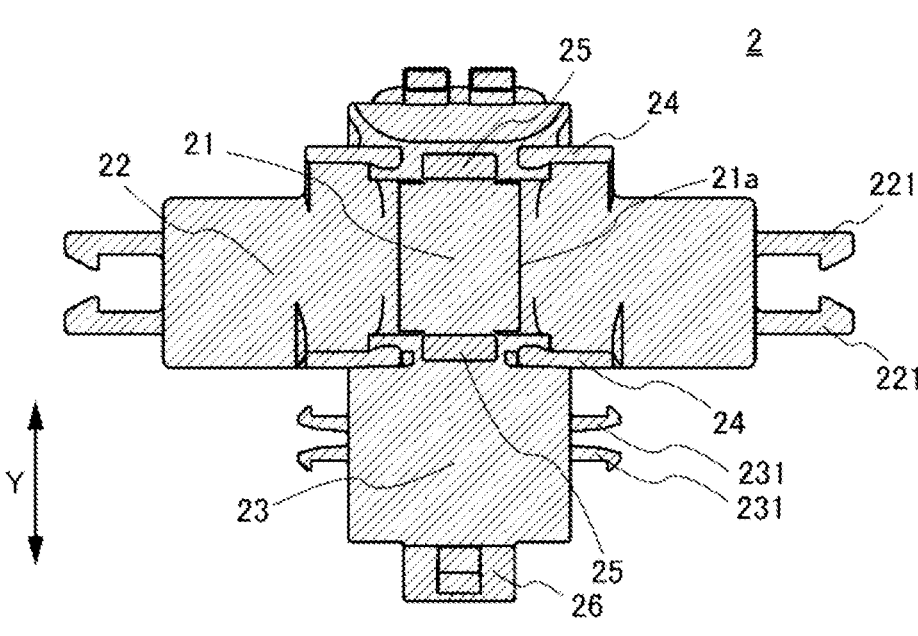
FIG. 5 is a front view of a second portion of the nasal adapter according to the embodiment of the presently disclosed subject matter.
Figure 5:
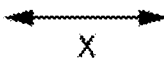

Next, the second portion 2 of the nasal adapter N will be described. As illustrated in a front view of FIG. 5, in the second portion 2, a column portion 21 is provided in a center of an upper portion, and a wing plate portion 22 is provided on the left and right sides thereof. The column portion 21 has an internal space due to its cylindrical shape, and its front surface is located forward of a front surface of the wing plate portion 22. As viewed from the front, the column portion 21 protrudes forward from the center of the wing plate portion 22. A body portion 23 is provided below the column portion 21. The body portion 23 has an internal space due to its arch-shaped shape protruding forward. The internal space of the body portion 23 communicates with the internal space of the column portion 21. Two upper fixing claws 221 are provided leftward from the wing plate portion 22 on the left side, and two upper fixing claws 221 are provided rightward from the wing plate portion 22 on the right side. Two lower fixing claws 231 are each provided from the body portion 23 toward the left direction and the right direction. A total of four projections 24 with substantially plate shapes protrude forward from upper and lower sides of right and left sides of the column portion 21 of the wing plate portion 22. Further, above and below the column portion 21, sensor engaging claws 25 protrude forward. The sensor S is positioned on the four projections 24 so as to straddle the column portion 21 and is attached between the two sensor engaging claws 25 by being engaged therewith. Exhaled breath is introduced into the internal space of the column portion 21. The column portion 21 is provided with window portions 21a with transparency on the left and right, and carbon dioxide concentration is measured from an amount of absorption of a specific wavelength in exhaled breath in the internal space of the column portion 21 by passing infrared rays from the sensor S.

Figure 6:
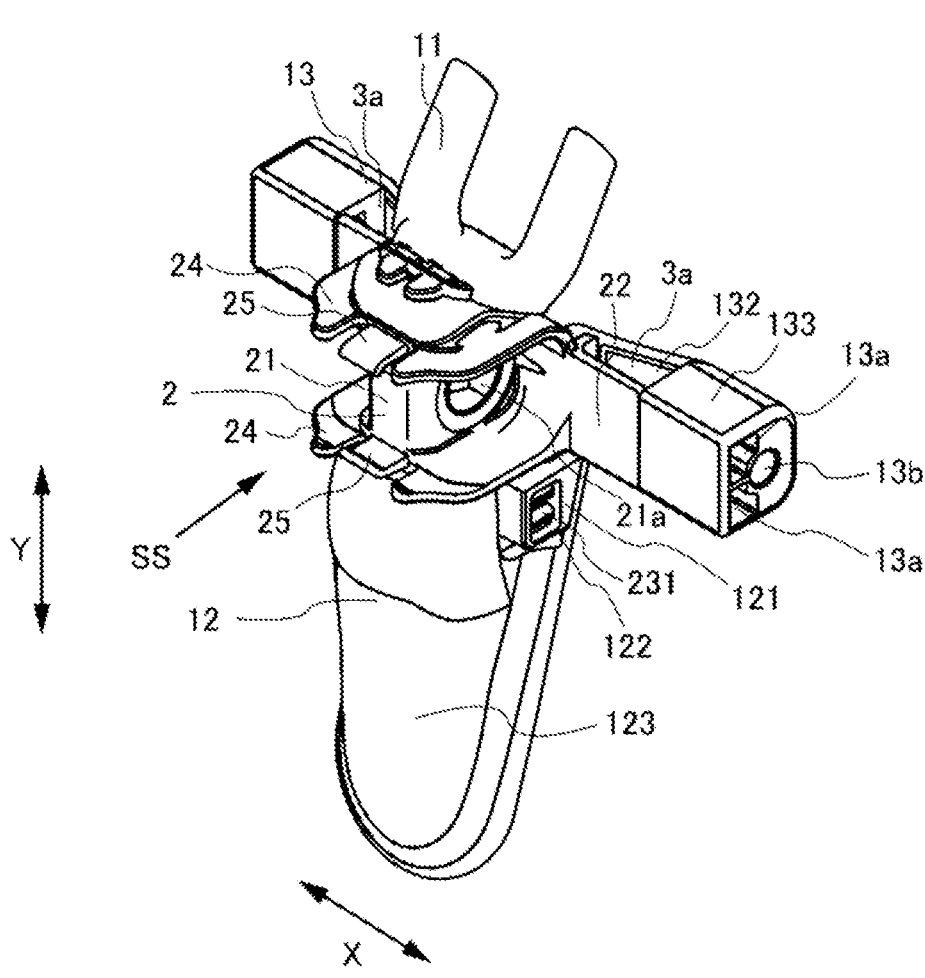
FIG. 6 is a perspective view of the nasal adapter according to the embodiment of the presently disclosed subject matter.

The first portion 1 and the second portion 2 are assembled and fixed together to form the nasal adapter N. When fixing, the four upper fixing claws 221 of the second portion 2 are fitted into the upper fixing holes 13a of the first portion 1. Also, the four lower fixing claws 231 are fitted into the two lower fixing holes 12a. Fitting is done using the flexibility of the first portion 1. FIG. 6 illustrates a perspective view of the assembled nasal adapter N. In FIG. 6, a portion around the second portion 2 corresponds to the first portion 1. By fitting the four upper fixing claws 221 of the second portion 2 into the upper fixing holes 13a of the first portion 1, the first portion 1 is fixed to the second portion 2 having rigidity so as to stretch from side to side. Also, the mouth exhalation guide portion 12 is fixed to the second portion 2 by attaching the four lower fixing claws 231 to the two lower fixing holes 12a.

A space between the supply back portion 132 of the first portion 1 and the wing plate portion 22 of the second portion 2 is vertically open to form the gas supply port 3a upward and the gas supply port 3b downward. FIG. 6 illustrates the gas supply port 3a. Although not illustrated in FIG. 6, the gas supply port 3b is located below the gas supply port 3a. The nasal cannula 5 is attached to the cannula hole 13b of the connection head 133 to supply gas. The gas supplied from the right and left changes its direction in the space between the supply back portion 132 and the wing plate portion 22, and then the gas is supplied to the vicinities of the nostril NT and the mouth M via the gas supply port 3a toward an upper direction and the gas supply port 3b toward a lower direction.

The sensor S having a U shape is attached in front of the second portion 2 so as to straddle the column portion 21 from a sensor set direction SS. The sensor S is interposed between two sensor engaging claws 25 and engaged between the projections 24 provided at four locations in front of the second portion 2. Infrared rays from the sensor S pass through the two window portions 21a provided on the sides of the column portion 21 and the exhaled breath guided to the internal space of the column portion 21, and an attenuation rate of a specific wavelength is obtained.

Figure 7:
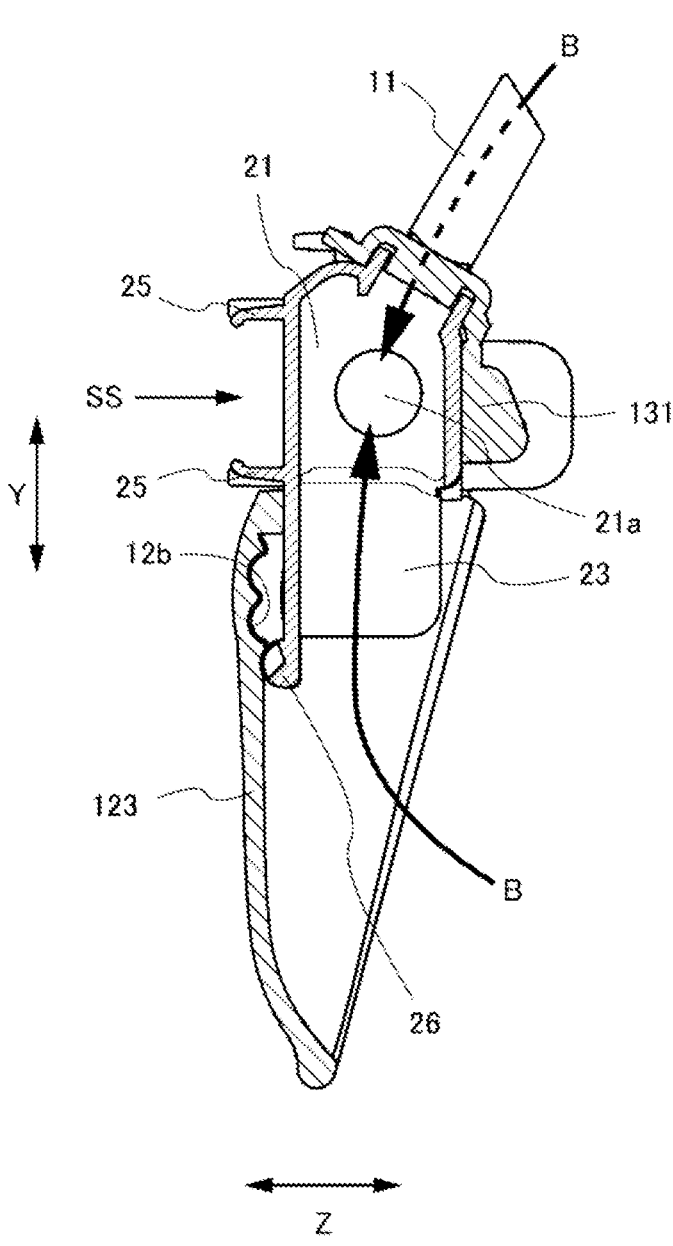
FIG. 7 is a longitudinal cross-sectional view of the nasal adapter according to the embodiment of the presently disclosed subject matter.

FIG. 7 illustrates a longitudinal cross-sectional view of the nasal adapter N taken along a plane perpendicular to the right-left direction X at the center of the right-left direction X. The column portion 21 of the second portion 2 is cylindrical and has an internal space. Also, the body portion 23 on the lower side has an arch-like shape and has an internal space. A lower end of the body portion 23 is provided with a convex portion 26 facing forward. A plurality of recess portions 12b are provided behind the facing portion 123. As illustrated in FIG. 3, the facing portion 123 is connected to the connecting section 121 fixed to the second portion 2 by the bendable portion 122. Therefore, when a surgeon applies force to the facing portion 123, the bendable portion 122 changes its bending and moves a position of the recess portion 12b with which the convex portion 26 engages. Then, the angle of the facing portion 123 with respect to the second portion 2 or the base portion 13 or the like of the first portion 1 can be changed. By changing the bend in the bendable portion 122, a posture of the facing portion 123 is changed, and a distance between the mouth M of the living body and the facing portion 123 is adjustable. The sensor S is mounted from the sensor set direction SS.

Exhaled breath B from the nostril NT reaches the internal space of the column portion 21 through a nasal-side guide path in the nasal exhalation guide portion 11. Also, exhaled breath B from the mouth M reaches the internal space of the column portion 21 from the rear of the facing portion 123 through a mouth-side guide path formed by the internal space of the body portion 23. In the internal space of the column portion 21, the gas concentration of the exhaled breath B is detected by the sensor S by infrared rays from the window portion 21a.

Next, operation of the embodiment will be described. First, as illustrated in FIG. 1, the nasal adapter N is fixed to the face F of the living body by the fixing band portion 6. In this case, the nasal adapter N is fixed so that the nasal exhalation guide portion 11 is inserted into the nostril NT and a curved concave side of the mouth exhalation guide portion 12 faces the mouth M.

Here, the second portion 2 is arranged so as to cover part of the base portion 13. The second portion 2 supports the base portion 13 and the mouth exhalation guide portion 12 by the upper fixing claw 221 and the lower fixing claw 231 illustrated in FIG. 5, and also supports the nasal exhalation guide portion 11 arranged on the base portion 13. Also, the postures of the nasal exhalation guide portion 11, the mouth exhalation guide portion 12, the base portion 13, and the cuttable portion 14, which are made of a flexible material, can be maintained. Therefore, the nasal exhalation guide portion 11, the mouth exhalation guide portion 12, the base portion 13, and the cuttable portion 14 can be integrally formed of a flexible material, and thus the number of components can be reduced to form the nasal adapter N with a simple configuration. Also, it is possible to prevent the nasal exhalation guide portion 11 and the mouth exhalation guide portion 12 from falling off the base portion 13. Further, by forming the mouth exhalation guide portion 12 from a flexible material, damage to a skin can be suppressed when the mouth exhalation guide portion 12 comes into contact with the living body.

Since the second portion 2 has higher rigidity than the nasal exhalation guide portion 11, the mouth exhalation guide portion 12, and the base portion 13, the nasal exhalation guide portion 11, the mouth exhalation guide portion 12, and the base portion 13 can be strongly supported.

In this way, the posture of the nasal exhalation guide portion 11 inserted into the nostril NT is maintained, and the posture of the mouth exhalation guide portion 12 arranged facing the mouth M is maintained. Subsequently, as illustrated in FIG. 7, the exhaled breath B exhaled from the nostril NT flows into the internal space of the column portion 21 from the nasal-side guide path in the nasal exhalation guide portion 11. Also, the exhaled breath B exhaled from the mouth M is guided by the rear surface of the facing portion 123 and the rear surface of the body portion 23 and flows into the internal space of the column portion 21 through the mouth-side guide path. Then, the sensor S measures the concentration of carbon dioxide contained in the exhaled breath B that has flowed in.

When the subject or the like wants to bring the facing portion 123 of the mouth exhalation guide portion 12 closer to the mouth M, a lower end of the facing portion 123 is moved backward. In this case, the bend at the bendable portion 122 changes and a space between the connecting section 121 and the facing portion 123 opens.

Then, as illustrated in FIG. 7, the position of the facing portion 123 is fixed by changing the position of the recess portion 12b of the facing portion 123 with which the convex portion 26 provided at the lower portion of the body portion 23 is engaged. As a result, the posture of the facing portion 123 is maintained, so that the posture of the facing portion 123 can be changed stepwise according to various shapes of the face F.

Here, when a surgeon determines that the facing portion 123 becomes an obstacle to an operation or the like, the connecting section 121 is removed from the lower fixing claw 231 and pulled. Then, the two cuttable portions 14 are torn off and cut, and the facing portion 123 can be removed. More specifically, when a finger is put in a rear side of the connecting section 121 illustrated in FIG. 4 and pulled outward, the cuttable portion 14 is torn off and the lower fixing claw 231 is pulled out from the lower fixing hole 12a. As a result, one connecting section 121 is removed from the second portion 2. Then, after cutting one cuttable portion 14, when the connecting section 121 is pulled toward the other connecting section 121 side, the other connecting section 121 is separated from the second portion 2, and the other cuttable portion 14 is also cut. Since the nasal exhalation guide portion 11 remains, the carbon dioxide concentration of the exhaled breath B from the nostril NT can be measured with the sensor S even after the facing portion 123 is removed.

The connecting section 121 is fixed to the second portion 2 by the lower fixing hole 12a. Further, the base portion 13 is fixed to the second portion 2 by the upper fixing hole 13a. Therefore, even when the cuttable portion 14 formed between the connecting section 121 and the base portion 13 is easily cut, it is difficult to cut when the connecting section 121 is fixed to the second portion 2.

Also, the bendable portion 122 that connects the connecting section 121 and the facing portion 123 is formed to be more difficult to cut than the cuttable portion 14. In the embodiment, the bendable portion 122 is thicker than the cuttable portion 14, as illustrated in FIG. 4 and the like. The facing portion 123 is not fixed to the second portion 2, but is connected to the connecting section 121 fixed to the second portion 2 by the bendable portion 122 that is difficult to cut, so the facing portion 123 will not come off the second portion 2 during normal use. When the connecting section 121 is removed from the second portion 2 and the facing portion 123 is pulled, it is cut at the cuttable portion 14 without being cut at the bendable portion 122.

In the embodiment described above, the nasal adapter N has the nasal exhalation guide portion 11, the base portion 13, the cuttable portion 14, and the mouth exhalation guide portion 12. However, the mouth exhalation guide portion 12 may be integrally connected to the base portion 13 by the cuttable portion 14, and the presently disclosed subject matter is not limited to the embodiment. For example, the nasal adapter N can be without the nasal exhalation guide portion 11 formed of the mouth exhalation guide portion 12, the base portion 13, and the cuttable portion 14. Also, in the embodiment, the first portion 1 and the second portion 2 are made of different materials and are separately formed and fixed, but they may be integrally formed. When integrally formed, they may be formed from the same material. In the embodiment, the facing portion 123 side of the cuttable portion 14 is fixed to the second portion 2, but it may be torn off immediately without being fixed.

In addition, in the embodiment, the bendable portion 122, the convex portion 26, the recess portion 12b, and the like are provided so that the angle of the facing portion 123 can be changed. However, a configuration in which the angle of the facing portion 123 can be changed by another structure may be adopted, or a configuration in which the angle of the facing portion 123 is not changed may be adopted. In the embodiment, the sensor S is attached to the nasal adapter N and used, but exhaled breath may be led from the nasal adapter N to a measurement device through a tube and measured.

By making the mouth exhalation guide portion integrally molded with the base portion, while maintaining the productivity of the product and the prevention of falling off during use, a user such as a surgeon can cut it with the cuttable portion as needed, remove the mouth exhalation guide portion from the base portion, and use the nasal adapter.

In addition, the specific configuration is not limited to the embodiment, and even when there is a change in design within a scope of the presently disclosed subject matter, it is included in the presently disclosed subject matter. Further, each of the above-described embodiments can be combined by utilizing each other's techniques unless there is a particular contradiction or problem in the purpose, configuration, or the like.

What is claimed is:

1. A nasal adapter comprising:
a first portion and a second portion, wherein
the first portion includes:
a mouth exhalation guide portion having a facing portion configured to face a mouth of a face of a living body and formed with a mouth-side guide path configured to guide exhaled breath exhaled from the mouth to the facing portion;
a base portion configured to be disposed above the mouth exhalation guide portion with respect to the living body; and
a cuttable portion integrally formed with the mouth exhalation guide portion and the base portion,
the cuttable portion disconnectably connects the mouth exhalation guide portion to the base portion,
the base portion is fixed to the second portion,
the first portion is detachable from the second portion at a connecting section below the cuttable portion with respect to the living body, and
wherein the cuttable portion has a notch configured to face toward the face of the living body in use.

2. The nasal adapter according to claim 1, wherein the cuttable portion is capable of being torn off due to thinness.

3. The nasal adapter according to claim 2, wherein the cuttable portion is formed to be narrower in a right-left direction with respect to the living body than portions of the mouth exhalation guide portion and the base portion near the cuttable portion.

4. The nasal adapter according to claim 1, wherein the cuttable portion connects the mouth exhalation guide portion to the base portion so as to be cuttable at two points, right and left, on an upper side of the mouth exhalation guide portion with respect to the living body.

5. The nasal adapter according to claim 1, wherein
connecting sections are provided on right and left sides of
the mouth exhalation guide portion with respect to the
living body, the connecting sections including the con-
necting section.

6. The nasal adapter according to claim 1, wherein
in the mouth exhalation guide portion, the connecting
section is provided near the cuttable portion.

7. The nasal adapter according to claim 1, wherein
the facing portion of the mouth exhalation guide portion
is connected to the connecting section by a bendable
portion on an opposite side of the connecting portion
from the cuttable portion, and
a posture of the facing portion is capable of being changed
by changing bending of the bendable portion to adjust
a distance between the mouth of the living body and the
facing portion.

8. The nasal adapter according to claim 7, wherein
the cuttable portion is formed to cut more easily than the
bendable portion.

9. The nasal adapter according to claim 1, wherein
the first portion and the second portion are separately
formed.

10

10. The nasal adapter according to claim 1, wherein
the first portion and the second portion are integrally
formed.

11. A nasal adapter comprising:
a first portion and a second portion which are integrally
formed, wherein
the first portion includes:
a mouth exhalation guide portion having a facing portion
configured to face a mouth of a face of a living body
and formed with a mouth-side guide path configured to
guide exhaled breath exhaled from the mouth to the
facing portion;
a base portion configured to be disposed above the mouth
exhalation guide portion with respect to the living
body; and
a cuttable portion integrally formed with the mouth exha-
lation guide portion and the base portion,
the cuttable portion disconnectably connects the mouth
exhalation guide portion to the base portion,
the base portion is fixed to the second portion, and
the first portion is detachable from the second portion at
a connecting section below the cuttable portion with
respect to the living body.

* * * * *